United States Patent
Fraser-Easton

(10) Patent No.: US 7,021,559 B2
(45) Date of Patent: Apr. 4, 2006

(54) PRESSURE REGULATING DEVICE FOR A PRESSURIZED DISPENSING VESSEL

(75) Inventor: Gilbert Fraser-Easton, Woodbridge (AU)

(73) Assignee: Primepak PTY LTD, Woodbridge (AU)

( * ) Notice: Subject to any disclaimer, the term of this patent is extended or adjusted under 35 U.S.C. 154(b) by 237 days.

(21) Appl. No.: 10/451,084

(22) PCT Filed: Jan. 30, 2003

(86) PCT No.: PCT/AU03/00092

§ 371 (c)(1),
(2), (4) Date: Jun. 19, 2003

(87) PCT Pub. No.: WO03/064286

PCT Pub. Date: Aug. 7, 2003

(65) Prior Publication Data

US 2004/0050880 A1    Mar. 18, 2004

(30) Foreign Application Priority Data

Jan. 31, 2002 (AU) ...................... PS0237

(51) Int. Cl.
    A62C 13/62    (2006.01)
    A62C 13/66    (2006.01)
    A62C 35/58    (2006.01)
(52) U.S. Cl. .................. 239/302; 222/396; 222/129.1; 222/135; 222/399; 239/31; 239/320; 137/509
(58) Field of Classification Search ................ 222/396, 222/302, 129.1, 135, 399; 239/302, 310, 239/320; 137/509
See application file for complete search history.

(56) References Cited

U.S. PATENT DOCUMENTS 5,110,012 A * 5/1992 Scholle et al. ............. 222/83.5

(Continued)

FOREIGN PATENT DOCUMENTS

EP    0 133 770       3/1985
EP    0 222 319 A2    5/1987

(Continued)

OTHER PUBLICATIONS

International Patent Application No. WO 99/44890, Didenkowski, Pressure Regualating Device for Pressurized Can, Sep. 10, 1999, all.*

*Primary Examiner*—David A. Scherbel
*Assistant Examiner*—James S. Hogan
(74) *Attorney, Agent, or Firm*—Stites & Harbison PLLC; Ross F. Hunt, Jr.

(57) ABSTRACT

A pressure regulating device for regulating pressure in a pressurized dispensing vessel, the device comprising a cartridge for storing pressurized fluid; the cartridge being sealed by a cap assembly having an expandable chamber and a flow passage for communicating fluid from the cartridge to the interior of the dispensing vessel; a closure member in the cap assembly to open and close the flow passage and an actuation means in the cap assembly to actuate the closure member, wherein the actuation means operates in response to expansion of the expandable chamber; and a one-way valve communicating the expandable chamber with the interior of the dispensing vessel via an aperture in the cap assembly, the valve having a resilient chamber seal in the expandable chamber extending across the aperture and restrained by chamber wall so to allow fluid to enter through the aperture and past the seal to charge the chamber to a predetermined pressure difference below the pressure in the dispensing vessel, and wherein expansion of the chamber occurs when the pressure in the dispensing vessel is lower than the pressure in the chamber.

18 Claims, 9 Drawing Sheets

U.S. PATENT DOCUMENTS 5,285,931 A * 2/1994 Alfons .................. 222/61
5,439,137 A    8/1995 Grollier et al.
6,412,688 B1 * 7/2002 Tucker et al. ............ 232/45

FOREIGN PATENT DOCUMENTS

| WO | WO 90/04129 | 4/1990 |
| WO | WO 99/44890 | 9/1999 |

* cited by examiner

Section A

Section B

Section C

Section D

Section E

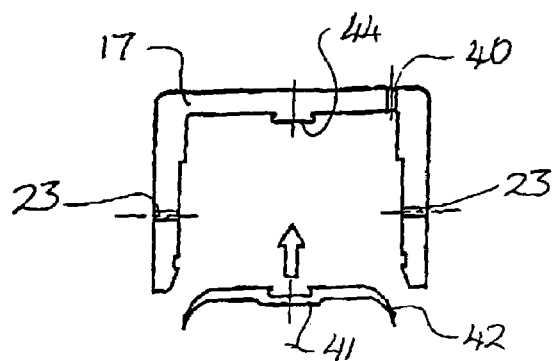
FIGURE 9
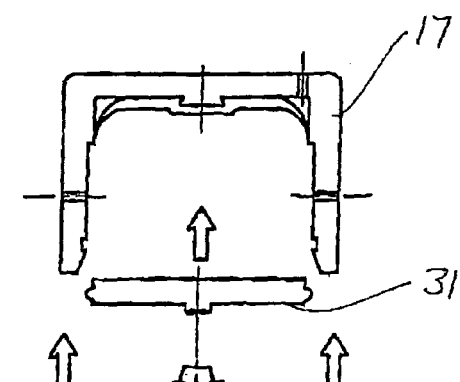
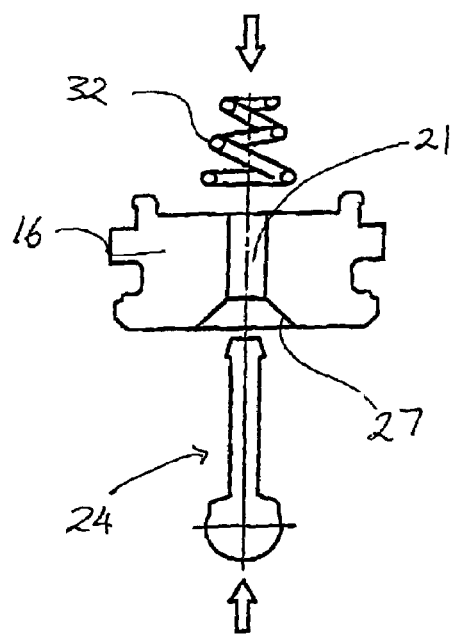
FIGURE 8
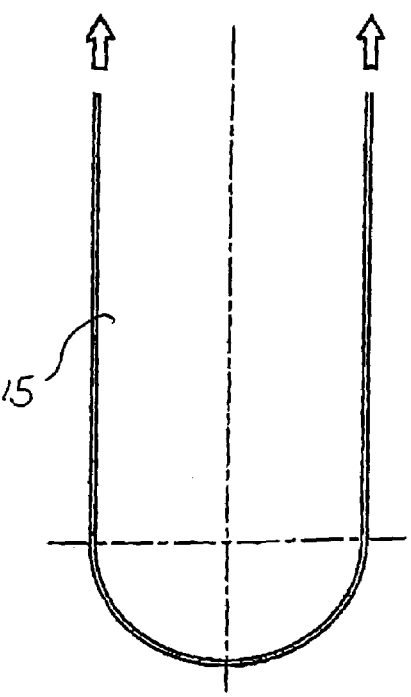
FIGURE 10

PRESSURE REGULATING DEVICE FOR A PRESSURIZED DISPENSING VESSEL

The present invention concerns a pressure regulating device for regulating a pressure within a pressurised dispensing vessel, such as an aerosol propellant or spray can.

BACKGROUND OF THE INVENTION

Dispensing liquid, and gas and powder products from a vessel under pressure provides a much greater force behind the dispensed spray stream than that achieved with the alternative spray pump. A drawback with pressurised aerosols is that the high spraying force in the cans is a result of using highly compressible hydrocarbons. It is well established that hydrocarbons are deleterious to the environment affecting the ozone layer and atmosphere in general. Furthermore, hydrocarbons are highly combustible and therefore dangerous if not used or disposed of thoughtfully.

A further drawback with pressurised cans and other vessels is that the can is pressurised once, only at filling, and hence provides the greatest dispensing pressure when the can is full but as the contents are reduced, and the pressure differential between the can interior and can exterior at atmospheric pressure is also reduced, the force behind the spray stream becomes weak. Difficulties are experienced with expelling low amounts of product remaining in the vessel.

Attempts have been made to maintain the interior of the vessel in a state of relatively constant pressure, that is over a constant non-decreasing pressure range, by providing a pressure regulating unit inside the vessel. The regulating unit is generally pressurised with the same gas with which the vessel is pressurised. These units are designed to release stored quantities of pressurised gas into the can interior as the can contents are dispensed from the can, thereby maintaining the pressure level inside the vessel for much longer. These known units are generally small in size comprising precisely manufactured components necessary to interact accurately.

Consequently, the pressure regulating units are often either improperly constructed failing frequently, or are too expensive to manufacture and unable to compete in price with regular aerosols or spray cans.

The main solution sought with the present invention is to provide a pressure regulating device that operates effectively in regulating pressure within a pressurised vessel but is also manufactured economically for producing a market competitive product.

SUMMARY OF THE INVENTION

According to the present invention there is provided a pressure regulating device for regulating pressure in a pressurised dispensing vessel, the device comprising:
  a cartridge for storing pressurised fluid;
  the cartridge being sealed by a cap assembly having an expandable chamber and a flow passage for communicating fluid from the cartridge to the interior of the dispensing vessel;
  a closure member in the cap assembly to open and close the flow passage and an actuation means in the cap assembly to actuate the closure member, wherein the actuation means operates in response to expansion of the expandable chamber; and
  a one-way valve provided in the expandable chamber, the one-way valve comprising an aperture communicating the expandable chamber with the interior of the dispensing vessel and a resilient chamber seal in the expandable chamber extending across the aperture and restrained by chamber walls so to allow fluid to enter through the aperture and charge the chamber to a predetermined pressure difference below the pressure in the dispensing vessel, and wherein expansion of the chamber occurs when the pressure in the dispensing vessel is lower than the pressure in the chamber.

The chamber seal of the one-way valve is preferably annular shaped with an upturned lip giving the seal a cup-like form. The seal preferably extends across the expandable chamber such that the lip bears against the walls of the chamber and seals the aperture from the chamber. A rib around the lip of the seal ensures good sealing. It is preferable that the predetermined pressure difference is dependent on the resilient seal which is ideally made to resist a pressure of approximately 1 to 10 psi and typically 2 to 5 psi, such that the seal will deform and allow fluid to enter through the aperture and into the chamber when the pressure in the dispensing vessel is greater than the chamber pressure by an amount equal to or greater than the pressure resistance of the chamber seal, and namely the predetermined pressure difference.

The pressurized fluid stored in the cartridge is preferably gas, and more specifically nitrogen or carbon dioxide.

The cap assembly preferably includes a cap cover on an inside end of which is a locating knob to locate the chamber seal. The cap cover is preferably attached to a neck plug to which the cartridge is crimped. The neck plug includes a neck passage to allow pressurised fluid in the cartridge to flow into the cap cover and out to the interior of the vessel through holes in the cover. The closure member is preferably a ball and stem cartridge valve which sits in the neck passage and is longitudinally moveable therein to open and close the passage.

The actuation means is preferably attached to the cartridge valve and comprises an annular resilient diaphragm extending across the cap cover and in sealing contact with the cover walls. The diaphragm forms the expandable wall of the expandable chamber and moves the cartridge valve into an open position in response to an expansion of the expandable chamber. A biasing means on the actuation means normally biases the cartridge valve in a closed position. The biasing means may be a return spring and specifically a coil spring.

According to the present invention there is further provided a method of assembling a pressure regulating device for insertion into a dispensing vessel for regulating pressure in the dispensing vessel when pressurised, the assembly including the steps of:
  assembling a cartridge with a sealing means to seal the cartridge interior, wherein the sealing means contains a closure member;
  with the closure member in an open position, pressurizing the cartridge with a fluid and closing the closure member to seal the cartridge interior when pressurised;
  locating a resilient chamber seal inside a cap;
  assembling an actuation means between the cap and the sealed cartridge, the actuation means actuating the closure member, and attaching the cap to the sealed cartridge wherein an expandable chamber is formed between the chamber seal and the actuation means, wherein the chamber seal is restrained by chamber walls and extends across an aperture in the cap to form a one-way valve into the expandable chamber, the actuation means being actuated by expansion of the expandable chamber; and while assembling the cap and actuation means, bleeding fluid from the expandable chamber to a pressure below that at which the dispensing vessel is to be pressurised.

The cartridge is preferably crimped onto the closure means whilst the sealed cartridge is snap-locked onto the cap.

The fluid in the expandable chamber is preferably bled to atmospheric pressure by inserting a tube in the cap aperture down past the seal to access the expandable chamber whilst the actuation means compresses the chamber during assembly.

The invention further provides a method of installing the pressure regulating device described above into a vessel to be pressurized whereby:

the device is inserted into an un-pressurised vessel containing product to be dispensed;

sealing the vessel by fitting an outlet valve on the vessel;

pressurizing the vessel with a gas thereby simultaneously pressurizing the expandable chamber to a predetermined pressure below the vessel pressure, the pressure difference dependent on the pressure resistance of the resilient seal.

BRIEF DESCRIPTION OF THE DRAWINGS

The present invention is described further by way of example with reference to the accompanying drawings by which:

FIG. 8 illustrates a first step in the assembly of the pressure regulating device;

FIG. 9 illustrates a second step in the assembly of the pressure regulating device;

FIG. 10 illustrates a third step in the assembly of the pressure regulating device;

DETAILED DESCRIPTION OF PREFERRED EMBODIMENT OF PRESENT INVENTION

Figure 1:
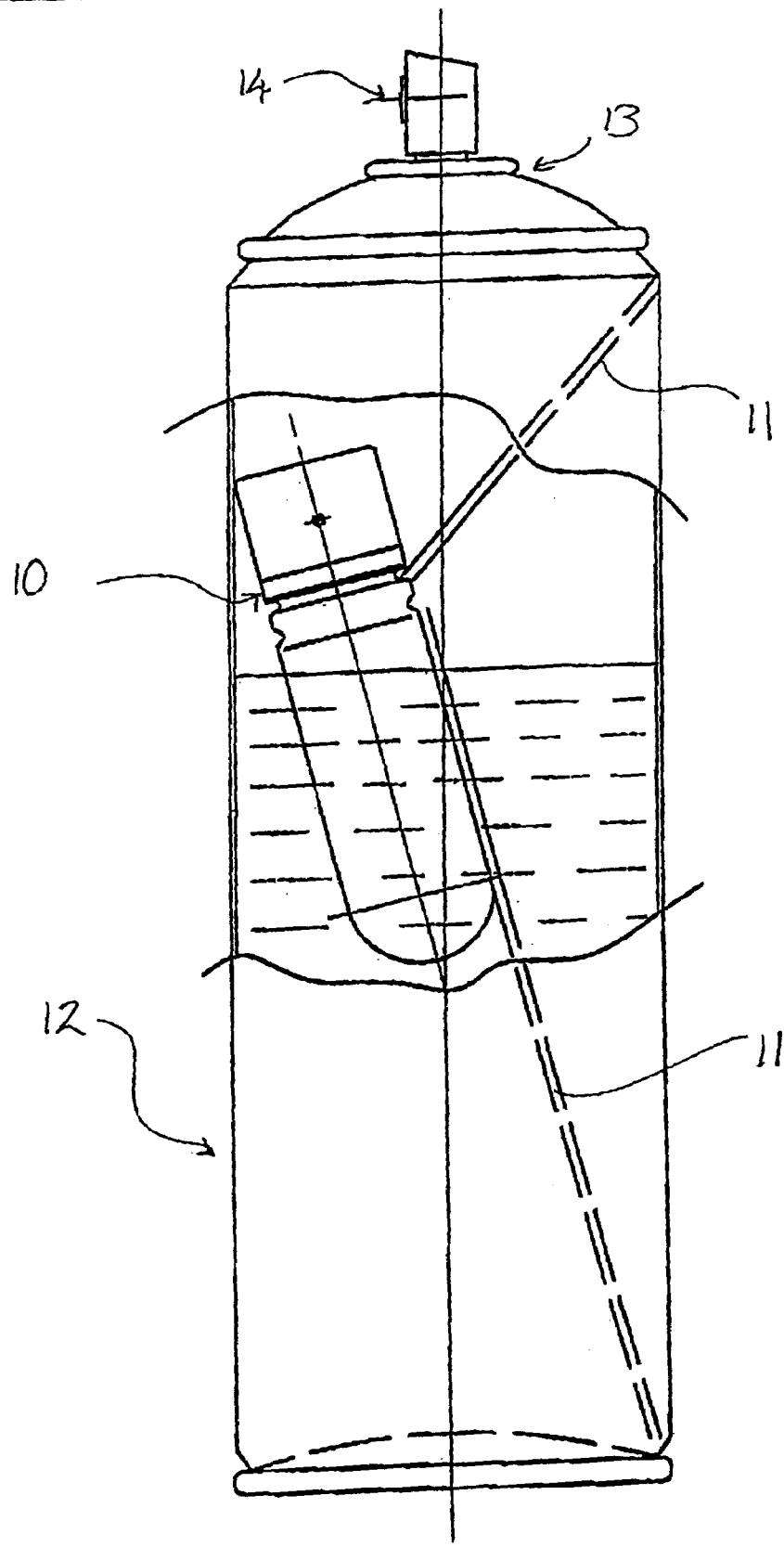
FIG. 1 is a part sectional view of a pressure regulating device according to the present invention located within a pressurised dispensing vessel.

The attached drawings illustrate several embodiments of a pressure regulating device adapted to be sit in a pressurized dispensing vessel to regulate vessel pressure during dispensation of the vessel contents and maintaining the pressure at a substantially constant range. The dispensing vessel may be in any form or size of pressurised vessel including aerosol cans, fire extinguishers and inhalers. In particular FIG. 1 illustrates the regulating device 10 restrained by ribs 11 inside a pressurised vessel 12, namely an aerosol can. The device is inserted in the vessel prior to pressurizing and after liquid or solid product has been added. The ribs keep the device above the product level. After insertion, the vessel is sealed by fitting at the top of the vessel 12 an outlet valve 13 carrying a spray nozzle 14. The vessel is then pressurised with a fluid, and typically with nitrogen or carbon dioxide gas.

The regulating device operates to release fluid, namely gas, stored under pressure when the pressure in the dispensing vessel drops to create a pressure differential with the device. Gas stored in the device is stored under a greater pressure than the gas in the dispensing vessel. Release of the gas in the pressure regulating device raises the pressure in the vessel back up to a desired value where it can dispense its contents with sufficient force.

Figure 2:
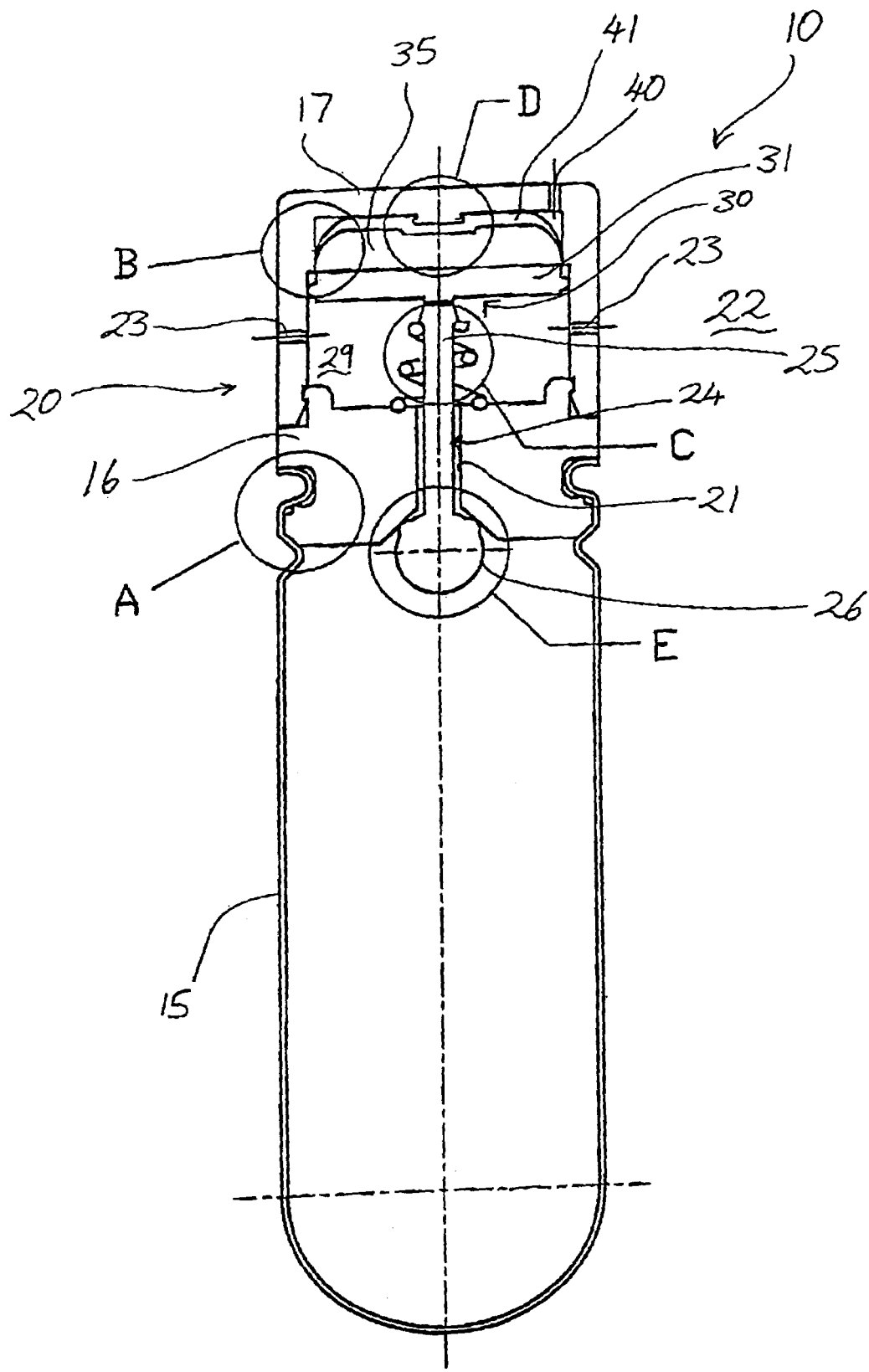
FIG. 2 is a side sectional view of a preferred embodiment of the pressure regulating device.

The regulating device, illustrated in more detail in FIG. 2, includes a cartridge 15 which stores under pressure the same gas contained in the pressurised vessel 12. The pressure of the compressed gas in the cartridge is determined by various factors including industry standards, the amount of product to be dispensed and the pressure necessary to dispense the product. By way of example, the gas stored by the cartridge can be stored at ten times the pressure of the gas stored in the dispensing vessel.

Figure 3:
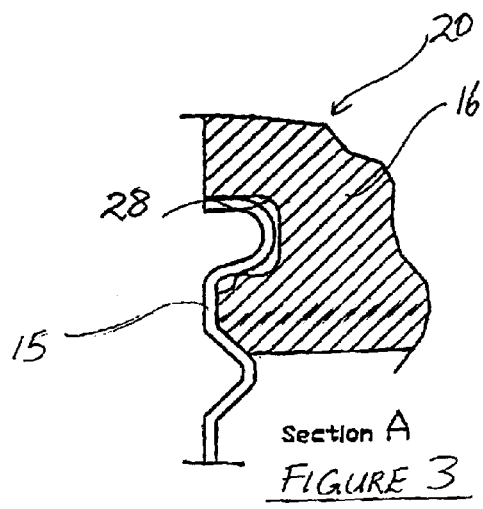
FIG. 3 is an enlarged view of Section A identified in FIG. 2.
Figure 7:
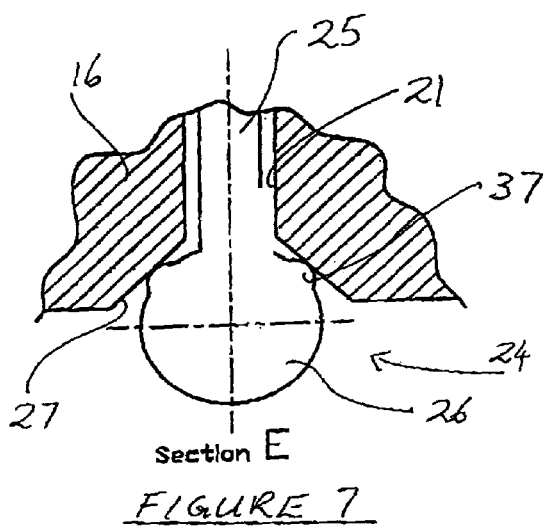
FIG. 7 is an enlarged view of Section E identified in FIG. 2.

The cartridge is crimped onto and sealed by a cap assembly 20, specifically comprising a neck plug 16, and a cap cover 17. The cartridge 15 is crimped onto the neck plug 16 which has annular groove provisions 28 into which the crimped section of the cartridge is crimped. This is best illustrated in the enlarged view of FIG. 3. A neck passage 21 through neck plug 16 provides access for pressurized gas in the cartridge 15 to flow into the cap assembly 20 and to the exterior 22 of the regulating device, and hence interior of pressurized vessel 12. The gas exits the cap assembly through a number outlet holes 23 disposed around the cap cover 17. Longitudinally movable within the neck passage 21 is a cartridge valve 24 of the ball and stem type. The stem 25 of the valve 24 extends through the passage 21 whilst the ball 26 of the valve abuts a valve seat 27 diverging from the neck passage 21 and limiting upward movement of the cartridge valve when viewed in FIG. 2. Annular ridge 37 on ball 26 improves sealing contact of the ball against the valve seat 27. FIG. 7 best illustrates this. A return spring 32 positioned over stem 25 and captured between neck plug 16 and a stop 38 at the end of stem 25 biases the valve 24 in a closed positioned that is, with the ball 26 bearing against the valve seat 27. The consistency of the pressure in the dispensing vessel is controlled by the pressure rating on the spring. Specifically, the closing force exerted by the spring can be calibrated to allow the cartridge valve to begin moving at a desired pressure differential between the dispensing vessel and regulating device.

Figure 4:
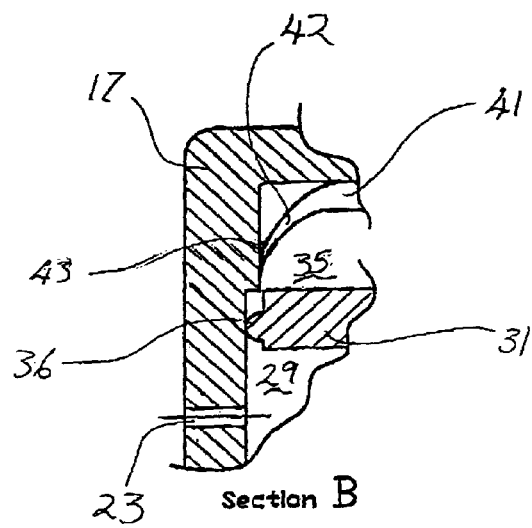
FIG. 4 is an enlarged view of Section B identified in FIG. 2.
Figure 5:
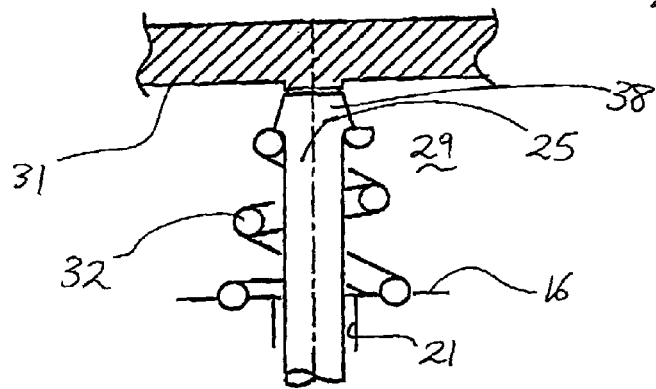
FIG. 5 is an enlarged view of Section C identified in FIG. 2.

The stem end of the cartridge valve is attached to an actuation means 30 comprising an annular resilient diaphragm 31. The diaphragm 31 extends across the inside of the cap cover 17 and sealingly contacts the walls of the cover, dividing it into two chambers: flow chamber 29 and expandable chamber 35. As seen in the corresponding enlarged view of the diaphragm edge, FIG. 4, an in-built annular rib 36 extending around the edge of the diaphragm ensures a sealing contact with the inside wall of cover 17. Located on the cartridge valve side of the diaphragm 31 is the flow chamber 29 through which the compressed gas in the cartridge flows on its way to the exterior of the device. On account of the open outlet holes 23 the pressure in the flow chamber 29 is therefore at the same pressure as the exterior of the device, that is, the same as the interior of the pressurised vessel. The return spring 32 is located in flow chamber 29 and normally biases the cartridge valve in a closed position. The spring 32 featured in FIGS. 2 and 5 is a coil spring, but any type of biasing means can be used. For example, the compression spring 33 illustrated in FIG. 13 comprises resilient arms 34 and is positioned between the stem 25 and diaphragm 31 to bias the cartridge in a closed position. Other spring types and elastic return means are also envisaged to be equally suitable, provided they function to bias the valve in a closed position.

Figure 6:
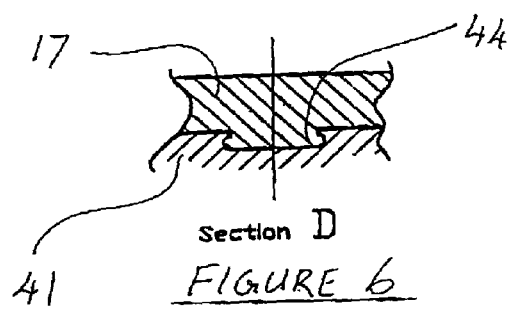
FIG. 6 is an enlarged view of Section D identified in FIG. 2.

On the other side of the diaphragm 31 to the flow chamber 29 is the expandable chamber 35 bound by the sealing diaphragm and the side and end walls of the cap cover 17. An aperture 40 in the end wall allows for communication between the chamber 35 and exterior of the device 22. A chamber seal 41 extending across the chamber and restrained by the chamber walls together with the aperture 40 forms a one-way valve into the chamber. Chamber seal 41 is annular in shape with an upturned lip 42 giving the seal a cup-like form. In the first embodiment the seal extends across the entire expandable chamber with the lip bearing against the walls of the chamber and sealing the aperture from the chamber. The chamber seal is positioned on a locating knob 44 as illustrated in FIG. 6. A rib 43 around the lip 42 of the seal provides an O-ring type wall contact and ensures good sealing. The seal is made of a resilient material that provides the seal with a pressure resistance. Specifically, the seal will only deform to allow fluid through the aperture 40 into chamber 35 when the difference in fluid pressure between the exterior of the device and the expandable chamber exceeds the seal's pressure resistance.

Figure 11:
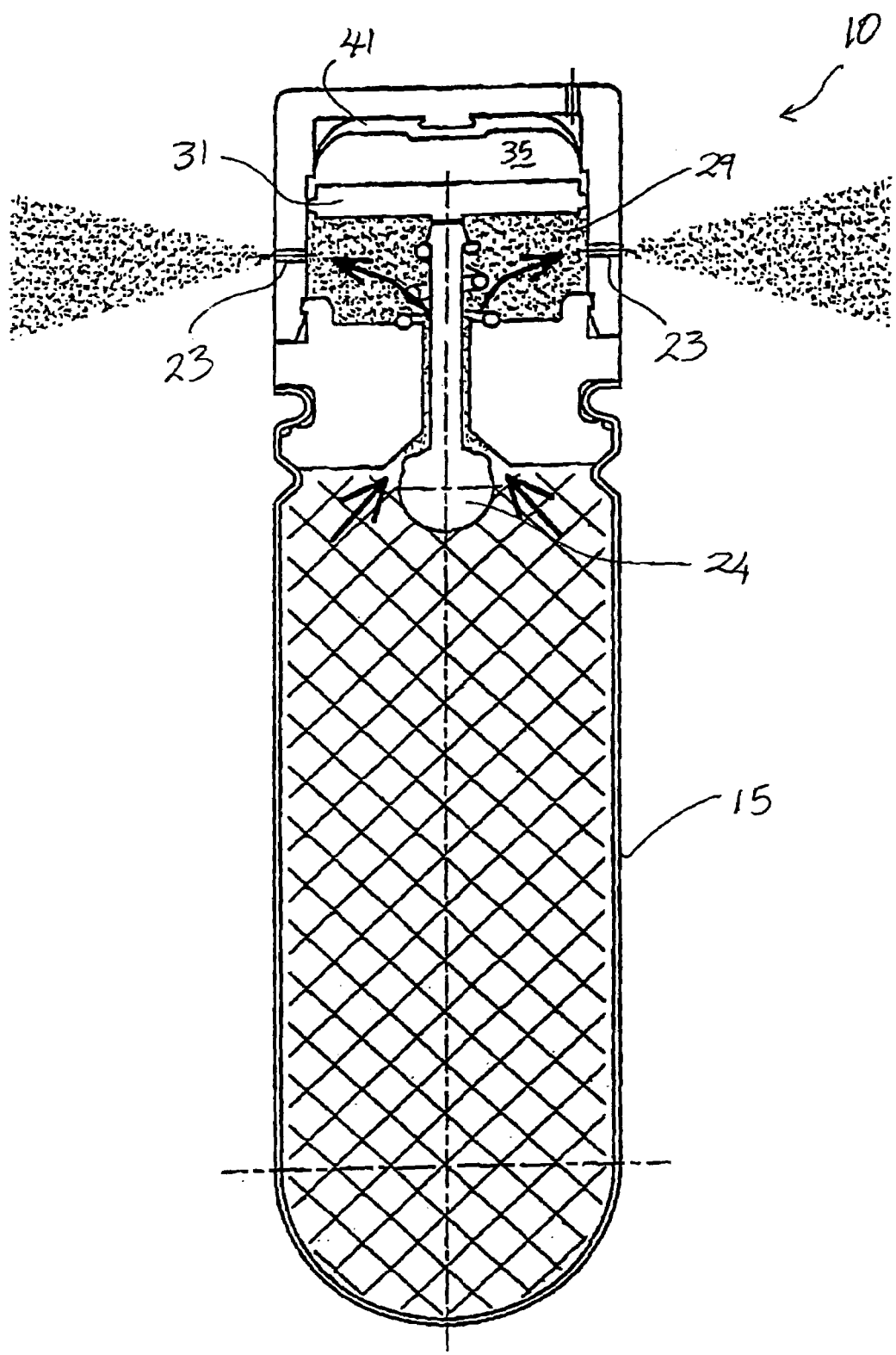
FIG. 11 illustrates the pressure regulating device in use.

The seal can operate with a pressure resistance of between 1 to 10 psi (6.895 kPa to 68.95 kPa), but the device 10 is more effective if the seal resistance is between 2 and 5 psi (13.79 kPa and 34.48 kPa). Accordingly, when the vessel is fully charged the pressure in the expandable chamber 35 will be less than that in the vessel depending on the seal resistance. For example, if the vessel is pressurised at 60 psi, and the chamber seal resistance in the pressure regulating device is 2 psi, then the pressure in the chamber 35 will pressurise to 58 psi. As the pressure in the vessel drops, owing to fluid product being dispensed through the spray nozzle, the pressure in the flow chamber 29 will also drop and come closer to the pressure of the expandable chamber 35. As the pressure in the flow chamber 29 drops below that in the expandable chamber, the pressure difference will cause the expandable chamber to expand urging the diaphragm 31 to move against the return spring to open the cartridge valve. The cartridge valve is moved against the resistance of the return spring to open the neck passage 21 and allow compressed gas stored in the cartridge 15 to immediately flow through the flow chamber 29 and outlet holes 23 and into the pressurised vessel 12. FIG. 11 illustrates the device operating to dispense gas in the direction of the arrows. As the vessel pressure increases as a result of the extra gas dispensed by the regulating device, the pressure returns to a level that will cause the diaphragm to move back towards the expandable chamber thereby moving the cartridge valve back into a closed position and closing the gas flow path. The regulating device operates in this manner until the product in the pressurised vessel is dispensed. The gas stored in regulating device is calculated to run out after the vessel's product is entirely dispensed. The outcome is a longer vessel life at a more consistent dispensing pressure.

FIGS. 8 to 10 illustrate how the regulating device 10 is assembled. Firstly, FIG. 8 shows the cartridge valve 24 being inserted through neck passage 21 in neck plug 16. This forms a cartridge sealing means for the cartridge 15. The return spring is positioned over the valve stem 25 at this stage to bias the cartridge valve in a closed position. The lower half of FIG. 10 illustrates the cartridge being assembled with the cartridge sealing means. At this stage the cartridge valve is opened and the cartridge is pressurised with the gas to a high pressure. As mentioned above, the gas pressure is dependent on several variables but, as a ball park estimate, may be about ten times the pressure of the pressurised vessel. The valve 24 is then allowed to close. Meanwhile, the chamber seal 35 is located on locating knob 44 in the end of cap cover 17. The pressurised and sealed cartridge is then assembled with the cap cover with the diaphragm 31 mounted therebetween.

To assemble the diaphragm between the sealed cartridge and cap cover the diaphragm is first mounted on the end of stem 25 of valve 24. The sealed cartridge with diaphragm is then brought together with cap cover 17 with the diaphragm being sealingly pushed into the cap cover, its edges in sealing contact with the cover. However, owing to the aperture 40 and chamber seal 41 forming a one-way valve in the cap cover, the diaphragm can not be inserted into the cap cover unless the one-way valve is opened. Accordingly, a tube is inserted through the aperture 40 and pushed past chamber seal 41 to access the expandable chamber 35 thereby bleeding the chamber of air as the diaphragm 31 is pushed into position. In order for a pressure differential to be created between the chamber 35 and the dispensing vessel interior 22, it is important that the pressure in chamber 35 is bled to below the pressure to which the pressurised vessel is to be charged. In practice, the chamber 35 pressure is bled to atmospheric pressure as the diaphragm is assembled.

With the regulating device 10 primed it is next inserted in an unsealed vessel 12 already supplied with liquid or powder contents. Upon sealing the vessel with an outlet valve 13 the spray nozzle 14 is depressed and the interior of the vessel 12 is pressurised with gas, typically nitrogen or carbon dioxide. As the pressure in the vessel increases during pressurizing the pressure in the flow chamber 29 and the expandable chamber 35 is also increased. However, whilst the final pressure in the flow chamber 29 equals the pressure in the dispensing vessel, the one-valve that is chamber seal 41 and aperture 40 cuts off to prevent fluid flowing into the expandable chamber when the pressure differential over the chamber seal reaches the predetermined pressure difference, the difference being dictated by the pressure resistance of the chamber seal 41.

Using the previous example, if a regulating device is used with a chamber seal 41 having a pressure resistance of 2 psi and the vessel is pressurised to 60 psi, the flow into chamber 35 will stop when the chamber reaches a pressure of 58 psi. The 2 psi difference is accounted for by the one-way valve and specifically the pressure resistance of seal 41. The seal may be made of any suitably resilient material such as rubber, neoprene or other elastomers. During operation of the device, the gas in the chamber remains trapped and the pressure remains constant. In this manner the chamber acts as a memory chamber or a benchmark chamber against which a pressure differential is created with the pressurised vessel.

Continuing with the above example, in use when the spray nozzle is depressed to dispense fluid contained in the vessel 12, the pressure in the vessel will drop. When the pressure in the vessel drops by 2 psi to 58 psi, the diaphragm is in equilibrium with the same pressure on either side of the diaphragm in expandable chamber 35 and flow chamber 29. With the pressure in the vessel dropping even further chamber 35 will begin to expand pushing diaphragm 31 against the force of return spring 32 to open the cartridge, thereby releasing stored gas into the vessel to raise the vessel pressure back up. The vessel pressure will not necessarily return to the original 60 psi but will remain at around 55–59 psi, or an even larger but controlled psi range, depending on the force of return spring 32 to maintain diaphragm 31 in a position closing cartridge valve 24.

Figure 12:
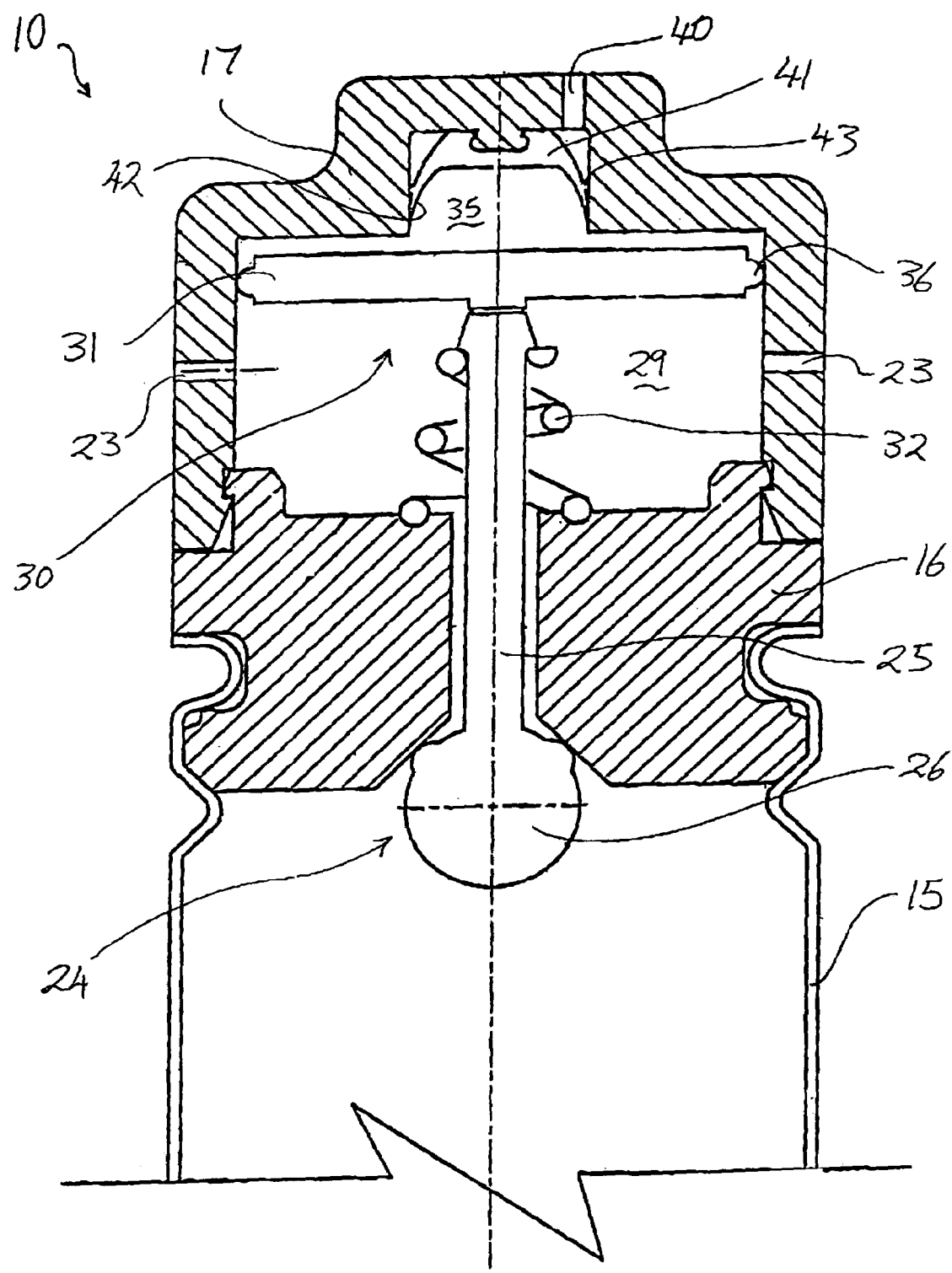
FIG. 12 is a part side sectional view of a pressure regulating device according to a second embodiment.

FIGS. 1 to 11 illustrate the expandable chamber 35 having a width comparable to the width of the diaphragm. However, the chamber 35 may be smaller and only extend part way across the diaphragm as illustrated in FIG. 12. Other variations on chamber shapes and sizes are foreseeable provided the diaphragm is still capable of responding to a pressure difference on account of the pressurised chamber.

Figure 15:
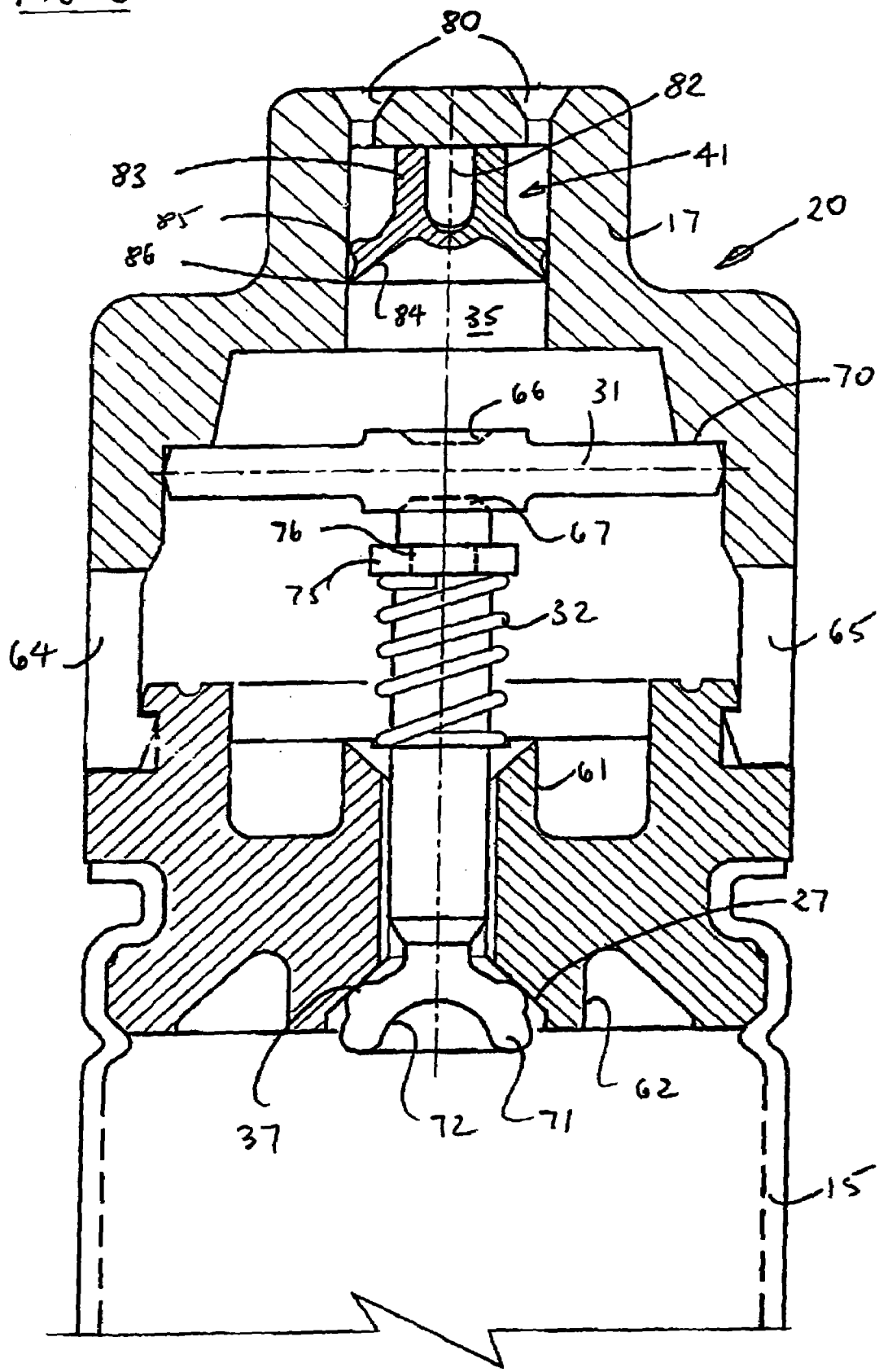
FIG. 15 is a part side sectional view of a pressure regulating device according to a third embodiment.

In the embodiment shown in FIG. 15 the gas cartridge assembly is similar to the assemblies illustrated in FIGS. 1 to 12 except that the neck plug 16 is molded in a more streamlined configuration to include annular indentations 61, 62 on the top and bottom surfaces. The cap assembly 20 clips on to the plug 16 in the same manner as FIGS. 1 to 12 but the outlet holes 23 are replaced by larger cutouts 64, 65 in the wall of the cap assembly 20. The diaphragm 31 has a pair of small central recesses 66, 67 in the top and bottom surface and the top periphery of the diaphragm 31 is arranged to press against the underside annular surface of a shoulder 70 on the inside of the cap 17. The base of the valve stem 25 has a hemispherical head 71 with an annular sealing rib 37. The head 71 includes a hemispherical cutout 72 on its underside. The valve stem 25 supports a coil spring 32 that is located by a spring retainer 75 that locates on a groove 76 in an upper portion of the valve stem 25. The spring 32, like the spring in the other embodiments, urges the valve to a closed sealed position with the valve seat 27 in the base of the plug 16.

This embodiment also includes a change in the construction of the cap cover 17 and chamber seal 41. In this embodiment the top of the cap cover has four equally spaced recessed fluid entry holes 80. A central lug 82 extends downwardly from the cap cover 17 and this is adapted to sit within a hollow cylindrical spigot 83 that forms part of the seal 41 which is in the form of a cup seal 41. The hollow spigot 83 joins a downwardly extending peripheral annular skirt 84 with an annular bead 85 that provides an upper sealing surface and a downwardly tapering lip 86 that provides a second lower sealing surface. As in the earlier embodiments, the expandable chamber 35 is defined between the cup seal 41 and the top of the diaphragm 31.

As in the other embodiments, the cup seal 41 acts as a one way valve allowing fluid into chamber 35 via the holes 80 and seals 84 and 85. Again, the seal 41 is designed to introduce a seal resistance of between 2 and 5 psi. Thus, when the vessel is fully charged the pressure in the expandable chamber 35 will be less than that in the vessel.

The principles used in the present pressure regulating device can be used to regulate pressures in vessels of varying sizes for a wide range of uses. For example, a larger version of the device could be used in regulating pressure inside a fire extinguisher. In fact, owing to the high level of pressure that can be stored by the present regulating device, it will be possible to make fire extinguishers smaller but still capable of dispensing the same amount of product. This is because the gas head space above the powdered product in fire extinguishers can be reduced because significant amounts of gas can be supplied from the regulating device. For vessels such as fire extinguishers it may be necessary that the regulating device stores gas compressed to a much higher pressure than, for example, aerosol cans. The wall thickness of the cartridge can be increased to withstand the high gas pressure therein. Generally with fire extinguishers, product is dispensed in one go so that the extinguisher is only available for a single use. With the present device installed in an extinguisher, product can be dispensed from the fire extinguisher at desired intervals and stopping and starting as many times as desired until the product runs out. Furthermore, since powder product used in fire extinguishers tends to collect at the bottom of an extinguishing vessel, the outflow from the present regulating device can be concentrated and directed by an outlet tube to expel gas at the bottom of a vessel and mix the powder content throughout the vessel.

Figure 13:
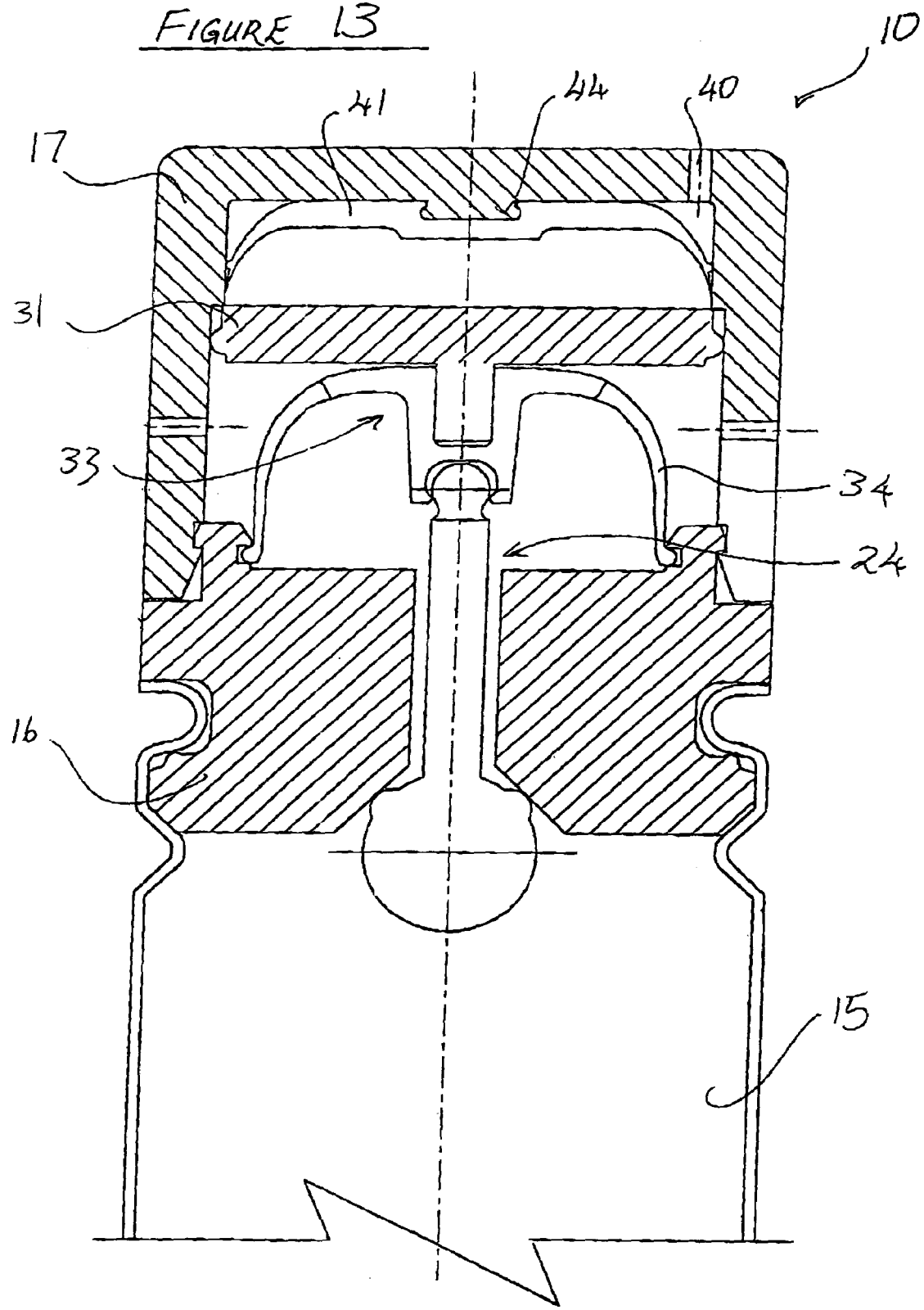
FIG. 13 is a side sectional view of a third embodiment of the pressure regulating device.
Figure 14:
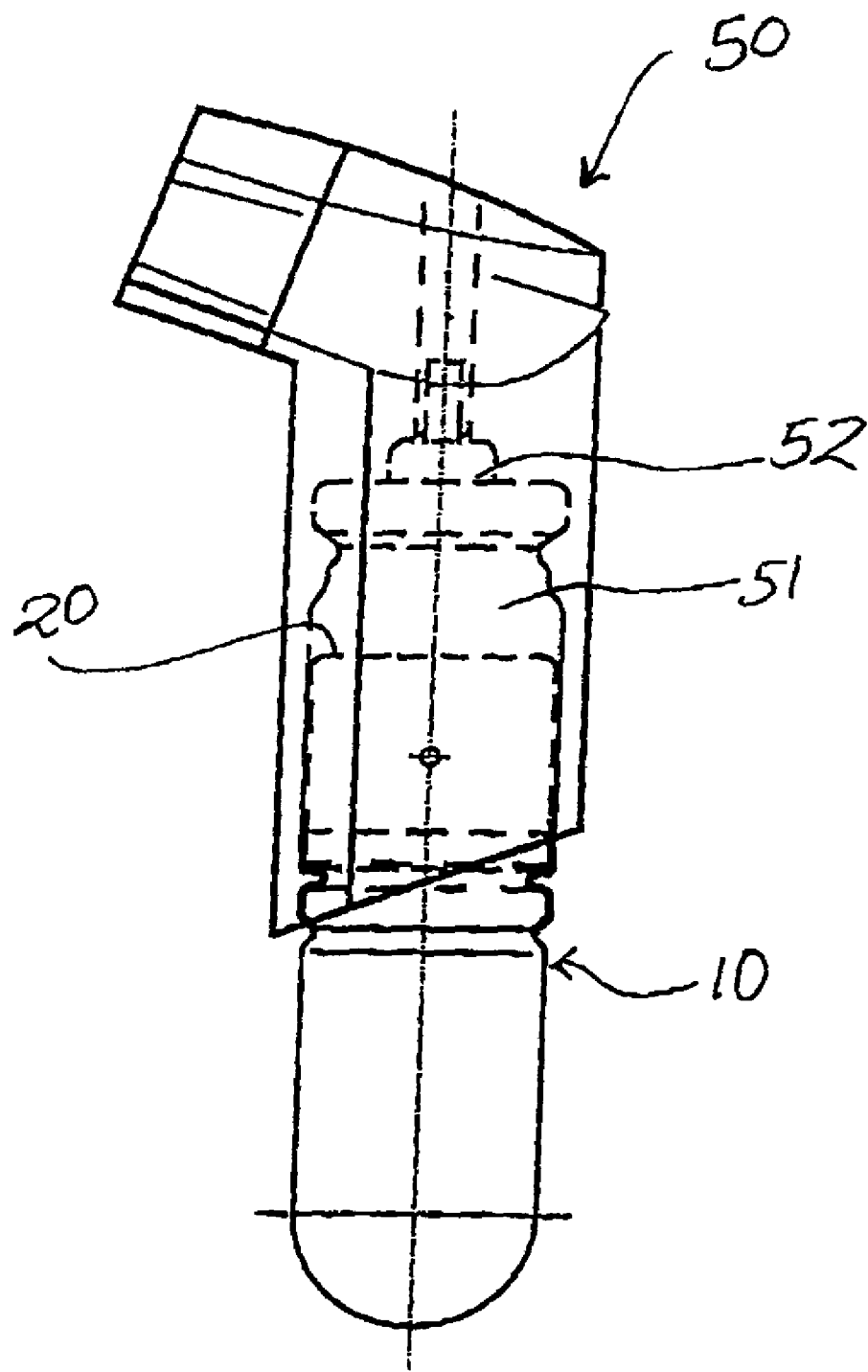
FIG. 14 illustrates another use of the pressure regulating device.

As illustrated in FIG. 13, the device can also be used in medical devices such as the Ventalin™ inhaler 50 pump for asthma sufferers illustrated. However, unlike the previous vessels described, the inhaler does not wholly contain the pressure regulating device. Rather, the device is attached to the inhaler body. Specifically, the pressurised section 51 of the inhaler 50 receives the cap assembly 20 of the regulating device and crimped onto the groove provisions 28 of the neck plugs 16 to form a sealed interior when the inhaler valve 52 is sealingly fitted to the top of the pressurised section 51. In this way, aperture 40 and outlet holes 23 all communicate with the inside of the pressurised vessel even though cartridge 15 is open to atmosphere. Attaching the present device to inhalers overcomes dispensing problems with regular inhalers where after a while users need to puff the inhaler several times to get the same amount of medicament dispensed in one puff with a new inhaler. Consequently users are not aware whether the dosage of medicament they are receiving is the correct amount.

Aside from inhalers, the pressure regulating device of the present invention can also be used with other medical devices such as transdermal medical devices or aerosols.

As described above, the pressure regulating device 10 can be either wholly contained within a pressurised vessel or partly attached to a pressurised vessel. To take this step further, the regulating device could be entirely separated from the pressurized vessel connected only by means of a tube and a collector cup that sealingly arranges over the cap assembly and specifically to capture the aperture and outlet holes. In this arrangement the present device can be used to regulate pressure in vessels pressurised at low pressures. For example, wine casks and beer kegs lose dispensing pressure as the contents of the cask or keg is dispensed. Connecting the present device to the cask or keg will maintain a relatively constant dispensing pressure. Similarly, the principle may be used to prevent aerated drinks, such an soft drinks, from going flat.

The construction of the present regulating device is suitable for manufacturing in large quantities at a cost effective rate. In combining inexpensive and reliable components such as effective interlocking casings and simple seals, the probability of failure is greatly reduced and the advantage of a cost competitive product is realised. The cost of the parts are themselves relatively inexpensive but so is the cost of tooling and assembling the product. Assembling the device, including charging the cartridge, involves a simple process and provides a product that can be directly inserted into an un-pressurised vessel with minimal fuss.

More importantly, the present pressure regulating device removes any need for using harmful hydrocarbons in pressurizing vessels. The difference in using other gases such as nitrogen and carbon dioxide over hydrocarbons is compensated by the present device and its capacity to store gas at high pressures. This provides for a more environmentally friendly product that is safer to manufacture, use and dispose. Furthermore, harmful hydrocarbons are commonly used to pressurise asthma inhalers. The present device removes all hydrocarbons from inhalers and other medicament dispensers, which research shows is harmful to the lungs.

It will be understood to persons skilled in the art of the invention that many modifications may be made without departing from the spirit and scope of the invention.

For the purposes of this specification it will be clearly understood that the word "comprising" means "including but not limited to", and that the word "comprises" has a corresponding meaning.

The invention claimed is:

1. A pressure regulating device for regulating pressure in a pressurized dispensing vessel, the device comprising:
    a cartridge for storing pressurized fluid; the cartridge being sealed by a cap assembly having an expandable chamber and a flow passage for communicating fluid from the cartridge to the interior of the dispensing vessel;
    a closure member in the cap assembly to open and close the flow passage and an actuation means in the cap assembly to actuate the closure member, wherein the actuation means operates in response to expansion of the expandable chamber; and
    a one-way valve communicating the expandable chamber with the interior of the dispensing vessel via an aperture in the cap assembly, the valve having a resilient chamber seal in the expandable chamber extending across the aperture, the chamber seal being of annular shape with a peripheral lip supported by an annular rib giving the seal a cup like form, wherein the peripheral lip and annular rib bear against a wall of the chamber so that the seal is restrained by a chamber wall so to allow fluid to enter through the aperture and past the seal to charge the chamber to a predetermined pressure difference below the pressure in the dispensing vessel, and wherein expansion of the chamber occurs when the pressure in the dispensing vessel is lower than the pressure in the chamber.

2. The pressure regulating device according to claim 1, wherein the seal extends across the expandable chamber.

3. The pressure regulating device according to claim 1, wherein the predetermined pressure difference is dependent on the resilient chamber seal which is made to resist a pressure of approximately 1 to 10 psi and typically 2 to 5 psi, such that the seal will deform and allow fluid to enter through the aperture and into the chamber when the pressure in the dispensing vessel is greater than the chamber pressure by an amount equal to or greater than the pressure resistance for the chamber seal.

4. The pressure regulating device according to claim 1, wherein the pressurized fluid stored in the cartridge is gas.

5. The pressure regulating device according to claim 4, wherein the gas is nitrogen or carbon dioxide.

6. The pressure regulating device according to claim 1, wherein the cap assembly includes a cap cover having the aperture and supporting the chamber seal.

7. The pressure regulating device according to claim 6, wherein the cap cover is attached to a neck plug to which the cartridge is crimped.

8. The pressure regulating device according to claim 7, wherein the neck plug includes a neck passage to allow pressurized fluid in the cartridge to flow into the cap cover and out the interior of the vessel.

9. The pressure regulating device according to claim 8, wherein the closure member is a valve which is biased to seat against the neck passage and is moveable therein to open and close the passage.

10. The pressure regulating device according to claim 9, wherein the actuation means is attached to the valve and comprises a resilient diaphragm extending across and in sealed contact with the interior of the cap cover.

11. The pressure regulating device according to claim 10, wherein the diaphragm forms an expandable wall of the expandable chamber and moves the valve into an open position in response to an expansion of the expandable chamber.

12. The pressure regulating device according to claim 11, wherein the valve has a stem that engages the diaphragm at one end with a head at the other that engages a seat defined by the neck passage, and biasing means urging the head to seat against the neck passage.

13. The pressure regulating device according to claim 12, wherein the biasing means is a return spring.

14. A method of assembling a pressure regulating device for insertion into a dispensing vessel for regulating pressure in the dispensing vessel when pressurized, the method including the steps of:
    assembling a cartridge with a sealing means to seal the cartridge interior, wherein the sealing means contains a closure member;
    with the closure member in an open position, pressurizing the cartridge with a fluid and closing the closure member to seal the cartridge interior when pressurized;
    locating a resilient chamber seal inside a cap;
    assembling an actuation means between the cap and the sealed cartridge, the actuation means actuating the closure member, and attaching the cap to the sealed cartridge wherein an expandable chamber is formed between the chamber seal and the actuation means, wherein the chamber seal is restrained by chamber walls and extends across an aperture in the cap to form a one-way valve into the expandable chamber, the actuation means being actuated by expansion of the expandable chamber; and
    while assembling the cap and actuation means, bleeding fluid from the expandable chamber to atmosphere.

15. The method according to claim 14, wherein the fluid in the expandable chamber is bled to atmospheric pressure by inserting a tube in the cap aperture down past the seal to access the expandable chamber whilst the actuation means compresses the chamber during assembly.

16. A method of installing the pressure regulating device in accordance with claim 1 into a vessel to be pressurized whereby:
    the device is inserted into an un-pressurized vessel containing product to be dispensed;
    sealing the vessel by fitting an outlet valve on the vessel;
    pressurizing the vessel with a gas thereby simultaneously pressurizing the expandable chamber to a predetermined pressure below the vessel pressure, the pressure difference being dependent on the pressure resistance of the resilient seal.

17. The pressure regulating device according to claim 1 wherein the expandable chamber has a neck of round cross section and the seal extends across the neck.

18. A pressure regulating device for regulating pressure in a pressurized dispensing vessel, the device comprising:
- a cartridge for storing pressurized fluid; the cartridge being sealed by a cap assembly having an expandable chamber and a flow passage for communicating fluid from the cartridge to the interior of the dispensing vessel;
- a closure member in the cap assembly to open and close the flow passage and an actuation means in the cap assembly to actuate the closure member, wherein the actuation means operates in response to expansion of the expandable chamber; and
- a one-way valve communicating the expandable chamber with the interior of the dispensing vessel via an aperture in the cap assembly, the valve having a resilient chamber seal in the expandable chamber to seal the aperture from the chamber, the chamber seal being of annular shape with a peripheral lip giving the seal a cup like form, whereby the peripheral lip bears against a wall of the chamber, the seal being restrained by the chamber wall to allow fluid to enter through the aperture and past the seal to charge the chamber to a predetermined pressure difference below the pressure in the dispensing vessel, the resilient chamber seal being made to resist a pressure of approximately 1 to 10 psi and typically 2 to 5 psi, such that the seal will deform and allow fluid to enter through the aperture and into the chamber when the pressure in the dispensing vessel is greater than the chamber pressure by an amount equal to or greater than the pressure resistance for the chamber seal and wherein expansion of the chamber occurs when the pressure in the dispensing vessel is lower than the pressure in the chamber.

* * * * *